United States Patent [19]

Parcell et al.

[11] 4,203,895

[45] May 20, 1980

[54] PROCESS FOR THE PREPARATION OF CIS-(±)-3,4-DIHYDRO-N,N,2-TRIMETHYL-2H-1-BENZOPYRAN-3-AMINE AND INTERMEDIATES PRODUCED THEREBY

[75] Inventors: Robert F. Parcell, Lakeland, Fla.; Ivan C. Nordin, Ann Arbor, Mich.

[73] Assignee: Warner-Lambert Company, Morris Plains, N.Y.

[21] Appl. No.: 896,403

[22] Filed: Apr. 14, 1978

[51] Int. Cl.$^2$ .................. C07D 230/02; C07D 311/04
[52] U.S. Cl. ............................. 260/239 E; 260/245.2
[58] Field of Search ......................... 260/345.2, 239 E

[56] References Cited

U.S. PATENT DOCUMENTS

| | | | |
|---|---|---|---|
| 3,607,886 | 9/1971 | Lockhart | 260/345.2 |
| 3,880,834 | 4/1975 | Kotera et al. | 260/239 E |
| 3,890,302 | 6/1975 | Kotera et al. | 260/239 E |
| 4,048,317 | 9/1977 | Watts | 260/345.2 |

FOREIGN PATENT DOCUMENTS 52-83829   7/1977   Japan ................................. 260/239 E

*Primary Examiner*—Nicky Chan
*Attorney, Agent, or Firm*—George M. Kaplan; Albert H. Graddis

[57] ABSTRACT

A process for the preparation of cis-(±)-3,4-dihydro-N,N,2-trimethyl-2H-1-benzopyran-3-amine (I), a known antidepressant, is disclosed. The process of the invention is a multi-step process starting with 2-methyl-2H-1-benzopyran (II), which involves the production of novel intermediates (2α,3β,4α)-(±)-3,4-dihydro-2-methyl-4-(methylamino)-2H-1-benzopyran-3-ol (IV) and its hydrogen sulfate ester (V) as well as (1aα,2β,7bα)-(±)-1,1a,2,7b-tetrahydro-1,2-dimethyl[1]benzopyrano[3,4-b]azirine (VI) and cis-(±)-3,4-dihydro-N,2-dimethyl-2H-1-benzopyran-3-amine (VII). In the final step of the process, compound VII is methylated to form compound I.

66 Claims, No Drawings

PROCESS FOR THE PREPARATION OF CIS-(±)-3,4-DIHYDRO-N,N,2-TRIMETHYL-2H-1-BENZOPYRAN-3-AMINE AND INTERMEDIATES PRODUCED THEREBY

BACKGROUND OF THE INVENTION

1. Field of the Invention

The present invention relates to a process for the production of cis-(±)-3,4-dihydro-N,N,2-trimethyl-2H-1-benzopyran-3-amine(I) and to certain intermediates used in the production thereof.

2. Description of the Prior Art

As disclosed by Lockhart, I. M., in U.S. Pat. No. 3,607,866, N,N,2-trimethyl-3-chromanamine, α-isomer (which is the cis-(±)-3,4-dihydro-N,N,2-trimethyl-2H-1-benzopyran-3-amine designated compound I in the subject invention) exhibits antidepressant activity. According to U.S. Pat. No. 3,607,866, N,N,2-trimethyl-3-chromanamine,α-isomer, and its acid addition salts may be produced by reacting 2-methyl-3-nitro-2H-1-benzopyran with lithium hydride and hydrolyzing the product to obtain 2-methyl-3-chromanamine,α-isomer and β-isomer from which the α-isomer is subsequently separated by a precipitation and recrystallization process. The α-isomer is then methylated to obtain the desired N,N,2-trimethyl-3-chromanamine.

In the U.S. Pat. No. 3,629,289, a related Lockhart patent, the α-isomer of 2-methyl-3-chromanamine intermediate and the process for its preparation are more fully described.

Bachman, et al. in J. Am. Chem. Soc. 70: 599–601 (Feb. 1948) disclose the preparation of 2-methyl-3-aminochroman by hydrogenation of 2-methyl-3-nitro-1,2-benzopyran using a Raney nickel catalyst.

In aforementioned U.S. Pat. No. 3,607,866 and in U.S. Pat. No. 3,629,289, the distinction between the α- and β-isomeric forms of the compounds prepared is discussed, particularly with respect to the physiochemical and pharmacological properties.

Lovgren, K., et al., in Acta. Pharm. Suecica 14:21–29 (1977) disclose the preparation of certain cis and trans 3-hydroxy-4-isopropylaminochromans starting with 6-methoxy-2H-chromen. Lovgren, et al. recognize that two completely different syntheses are required to obtain the cis and trans isomeric configurations. Intermediates formed during the synthesis of the trans isomers include trans-3,4-dibromo-6-methoxychroman and trans-3-bromo-4-hydroxy-6-methoxychroman. However, since none of the Lovgren compounds have a 2-methyl substituent, this reference is concerned only with isomerism at the 3,4-position of the chroman ring. In the instant invention, the 2-methyl substituent presents additional isomeric possibilities which are not considered in the Lovgren, et al. reference.

The preparation, isomeric configuration and pharmacological properties of related aminochroman derivatives are discussed in the following references: Huckle, et al., J. Med. Chem.12:277–279 (1969); Lockhart, et al., J. Med. Chem. 15: No. 8, 863–865 (1972); Sarda, et al., C.R. Acad. Sc. Paris 279: 281–4 (Aug. 12, 1974); Sarda, et al., Eur. J. Med. Chem. 11: No. 3,251–257 (May-June, 1976); and Sarda, et al., Eur. J. Med. Chem. 11: No. 3,257–262 (May-June, 1976).

In Japanese 52-083-829 (Takeda Chemical Industries) ring opening of an azirine derivative is achieved by hydrolysis: 5,6-dihydroxy-1,1α,2,3,4,8b-hexahydro-benzo[3,4]cyclohepta[1,2-b]azirine is hydrolyzed to form 1,2,5-trihydroxy-6-isopropylamino-6,7,8,9-tetrahydro-5H-benzocycloheptane hydrobomide, a useful remedy for asthma. The azirine derivative of the sixth reaction step of the instant invention involves a different ring system and ring opening is achieved by means of catalytic hydrogenation.

DESCRIPTION OF THE PARTICULAR EMBODIMENTS

According to this invention, a novel process for the production of cis-(±)-3,4-dihydro-N,N,2-trimethyl-2H-1-benzopyran-3-amine(I):

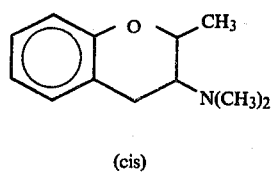

(cis)

is initiated by reacting compound II:

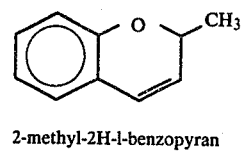

2-methyl-2H-1-benzopyran in water and a nonreactive, water-miscible solvent with bromine to obtain, in situ, compound IIa:

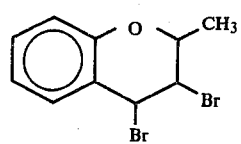

3,4-dibromo-3,4-dihydro-2-methyl-2H-1-benzopyran

In this first step of the process, the preferred solvent is tetrahydrofuran and the temperature of the reaction is maintained at about 7° C.–10° C. for about 45 minutes.

In the second step of the process, the reaction mixture containing compound IIa is treated with water and heated at reflux temperature for from about 5 minutes to about 3 hours, followed by neutralization with alkali such as aqueous sodium hydroxide, to obtain compound III:

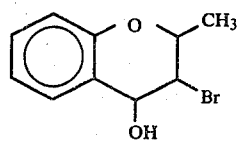

3,4-dihydro-3-bromo-2-methyl-2H-1-benzopyran-4-ol

In the third step of the process, compound III is dissolved in water or a water-miscible solvent and reacted with an aqueous solution of methylamine, while maintaining the temperature below about 25° C. to form, in situ, compound IIIa:

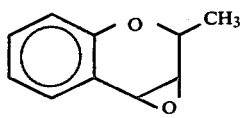

3,4-epoxy-2-methyl
benzopyran

Suitable solvents include water, lower alkanols such as methanol and ethanol; water-miscible ethers such as diglyme and dioxane; and mixtures thereof. The preferred solvent is methanol. At least 2 molar equivalents of methylamine per mole of compound III are required, with a moderate to large excess of methylamine being preferred.

The reaction mixture containing compound IIIa is refluxed for from about one hour to about 48 hours. Preferably, this phase of the reaction is conducted at from about 20° C. to about 30° C. for from about 16 to about 30 hours. The product of the reaction, compound IV, may be isolated by conventional means such as evaporation, followed by crystallization:

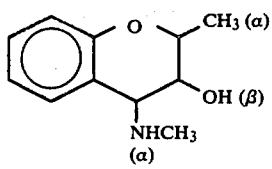

$(2\alpha,3\beta,4\alpha)$-($\pm$)-3,4-dihydro-
2-methyl-4-(methylamino)-2H-
1-benzopyran-3-ol In the fourth step of the process, sulfuric acid is dissolved in a hydrocarbon solvent or in a halogenated hydrocarbon solvent and treated with compound IV to obtain compound V:

![V structure]

$(2\alpha,3\beta,4\alpha)$-($\pm$)-3,4-dihydro-2-
methyl-4-(methylamino)-2H-1-
benzopyran-3-ol, hydrogensulfate
ester Suitable solvents in this fourth step of the process include hydrocarbons such as toluene and xylene; chlorinated hydrocarbons such as tetrachloroethane and chlorobenzene; and mixtures of these. The preferred solvent is xylene. The reaction mixture is conveniently heated at reflux under a water separator until water is no longer collected. Reflux temperatures above 110° C. are desirable. At 135° C. to 145° C., the reaction goes to completion in about one to three hours. A slight excess of either reactant may be used, but approximately equal molar amounts of reactants are preferred. Compound V may be isolated by conventional means such as crystallization.

In the fifth step of the process, compound V is heated with a strong base, i.e., an alkali metal hydroxide, preferably sodium hydroxide, to obtain compound VI:

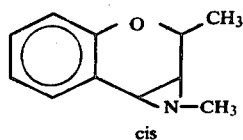

$(1a\alpha,2\beta,7b\alpha)$-($\pm$)-1,1a,2,7b-
tetrahydro-1,2-dimethyl[1]-
benzopyrano[3,4-b]azirine At least two molar equivalents of base are required per mole of sulfate ester V, with an excess being preferred. While additional organic solvent is unnecessary in this step of the process, a two phase system of aqueous alkali and a water-immiscible, nonreactive organic solvent is desirable; toluene is the preferred organic solvent. The temperature of the reaction is not critical but, when toluene is used as the organic solvent, a temperature of 95° C.–100° C. for from about 2 to about 4 hours is preferred. Compound VI may be isolated by conventional means, such as evaporation of the organic phase.

In the sixth step of the process of this invention, a solvent solution of compound VI is subjected to catalytic hydrogenation to effect ring opening and formation of compound VII:

![VII structure]

cis-($\pm$)3,4-dihydro-N,2-
dimethyl-2H-1-benzopyran-
3-amine

Suitable solvents for the step 6 hydrogenation reaction include hydrocarbon solvents such as benzene, toluene and xylene; lower alkanols such as methanol and ethanol; ethers such as tetrahydrofuran, dioxane and diglyme; and mixtures of these. For the hydrogenation, Noble metal catalysts such as platinum or palladium, and oxides thereof, may be used, optionally supported on a carbonacious carrier such as charcoal. The preferred hydrogenation catalyst is palladium on a charcoal carrier. Hydrogen pressure during the hydrogenation is not critical and pressures of from 15 to 150 pounds per square inch are suitable. The hydrogenation is normally carried out at ambient temperature until hydrogen uptake ceases. Generally, one mole of hydrogen is required for complete conversion of one mole of the azirine compound VI to compound VII. Compound VII may be isolated by standard procedures such as evaporation of solvent. Compound VII may also be isolated as a salt by reaction of the base with a suitable acid.

In step seven of the process, a solvent solution of compound VII is methylated to obtain the desired compound I. The methylating agents include methyl halides, particularly methyl iodide, dimethyl sulfate; methyl sulfonates, such as methyl methanesulfonate and methyl p-toluenesulfate; formaldehyde-formic acid mixtures; formaldehyde and hydrogen in the presence of a noble metal catalyst; and trimethyloxonium salts, such as trimethyloxonium tetrafluoroborate, trimethyloxonium tetrachloroferrate, trimethyloxonium hexafluoroantimonate and trimethyloxonium tetrachloroaluminate. When using the methyl halides, the methyl sulfonates, dimethyl sulfate or trimethyloxonium salts as the methylating agent, the reaction is preferably carried out in the presence of a base such as potassium carbonate, sodium carbonate or sodium bicarbonate. The preferred methylating agent is a formaldehyde-formic acid mixture.

When using the preferred formaldehyde-formic acid methylation procedure, excess formic acid serves as the solvent for reaction and additional solvent is neither necessary nor desirable. With other methylating agents, a variety of solvents may be used. These include hydrocarbons such as benzene, toluene and xylene; ether such as diethyl ether, dioxane, tetrahydrofuran and diglyme; lower alkanols such as methanol, ethanol and 2-propanol; lower alkanones such as acetone and 2-butanone (with the exception that the lower alkanone solvents are not used in hydrogenations with formaldehyde); tertiary amides such as dimethylformamide and N-methyl-2-pyrrolidinone; and mixtures of the aforementioned solvents.

The temperature and duration of the methylation reaction of step seven are not critical. In general, the reaction may be carried out at temperatures of from 10° C. to 150° C. or at the reflux temperature of the solvent for from 20 minutes to 48 hours. The longer the reaction times are necessary when lower temperatures are utilized. Using the preferred formaldehyde-formic acid methylation procedure, a temperature of from about 40° C. to 100° C. for from about 30 minutes to 6 hours is suitable. Generally, one mole of methylating agent is required per mole of secondary amine final product (V). When using the preferred formaldehyde-formic acid methylation procedure, a substantial excess of methylating agent is desirable. The final product, compound I may be isolated as the free base or as a salt by standard procedures.

The starting material, 2-methyl-2H-1-benzopyran (compound II) used in the novel process of the invention is known and described by Ursula Koch-Pomeranz, et al. in Helv. Chim. Acta. 56: 2981 at 2986 (1973) wherein this starting material is prepared starting from 1'-methylpropargyl phenyl ether.

The novel process of this invention is an improvement over previously known methods for preparing compound I in that certain hazardous intermediates required in the prior art processes are avoided. In addition, there is a substantial reduction in costs of starting materials and in the processing technique required.

The final compound I, prepared according to the process of this invention, is described in U.S. Pat. No. 3,607,886 as having antidepressant activity as evidenced by positive results obtained in certain pharmacological assays: compound I has been found to cause a significant suppression of hyper-irritability in rats following doses of 12.5 to 100 mg/kg, administered interperitoneally; and compound I was found to suppress the mouse-killing instinct in killer rats when administered at a dose of 15 mg/kg, administered interperitoneally.

Thus, compound I is indicated in the management of certain mental states such as depression when administered parenterally or orally to mammals.

For administration, compound I may be formulated according to methods well known to the pharmacists' art. Typically, saline solutions of compound I are used for injectable purposes. For oral administration, compound I may be administered in a saline solution or may be formulated with excipients such as lactose into tablets suitable for oral administration.

In order to further illustrate this invention, the following examples are provided.

EXAMPLE 1

(2α,3β,4α)-(±)-3,4-Dihydro-2-methyl-4-(methylamino)-2H-1-benzopyran-3-ol

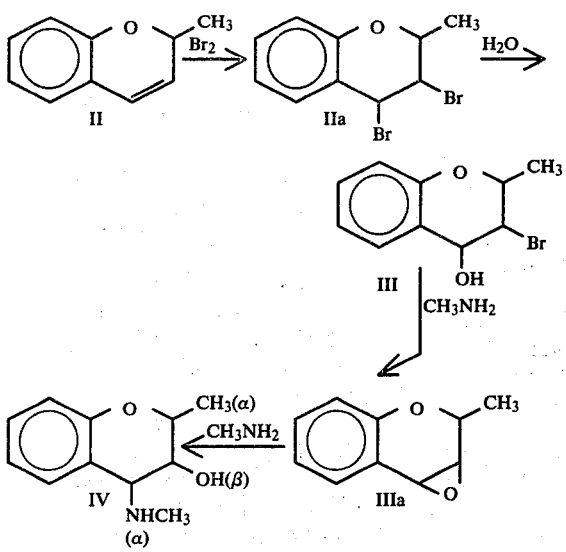

A stirred solution of 149.3 g. of 2-methyl-2H-1-benzopyran in 750 ml. of tetrahydrofuran and 72 ml. of water is cooled to 8° C. and treated dropwise with 162 g. of bromine over a 45 minute period while maintaining the temperature at 7°-10° C. There is then added 144 ml. of water and the solution is stirred and heated at reflux for 1 hour. The stirred solution is cooled and treated with 64 g. of 50% aqueous sodium hydroxide while maintaining the temperature at 10°-15° C. The resulting aqueous phase is separated and discarded. The organic phase is treated with 100 ml. of water and the mixture is stirred and heated at reflux for 2.75 hours. The mixture is then evaporated at reduced pressure to remove tetrahydrofuran and the aqueous residue of 3,4-dihydro-3-bromo-2-methyl-2H-1-benzopyran-4-ol (melting point, 77°-79° C.) is dissolved in 600 ml. of methanol. The methanol solution is stirred and treated slowly with 300 ml. of 40% aqueous methylamine while maintaining the temperature below 25° C. The resulting solution is stirred slowly at 20°-25° C. for 24 hours, heated at reflux for 1 hour and evaporated at reduced pressure to remove methanol. The aqueous residue is treated with 100 g. of sodium hydroxide and the mixture is extracted with three 200 ml. portions of toluene. The toluene extracts are combined and the solution is extracted with excess 6 N hydrochloric acid. The aqueous acid extract is basified with excess 50% aqueous sodium hydroxide and extracted with three 200 ml. portions of toluene. The toluene extracts are combined and the solution is treated with activated charcoal and anhydrous magnesium sulfate, and filtered. The filtrate is evaporated at reduced pressure and the residue of (2α,3β,4α)-(±)-3,4-dihydro-2-methyl-4-(methylamino)-2H-1-benzopyran-3-ol is crystallized from xylene; m.p. 110°-113° C.

EXAMPLE 2

(2α,3β,4α)-(±)-3,4-Dihydro-2-methyl-4-(methylamino)-2H-1-benzopyran-3-ol, Hydrogen Sulfate Ester

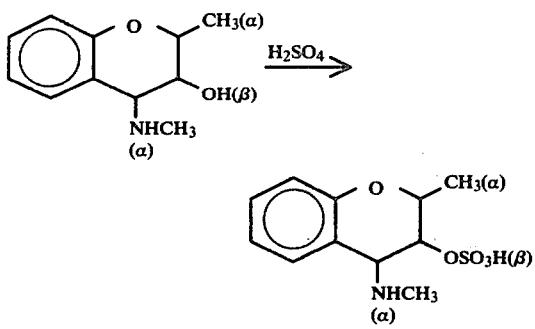

A mixture of 54.5 g. of 96% sulfuric acid and 800 ml. of xylene is stirred vigorously and treated portionwise with 103 g. of finely divided (2α,3β,4α)-(±)-3,4-dihydro-2-methyl-4-(methylamino)-2H-1-benzopyran-3-ol (Example 1) over a period of 10 minutes. The mixture is stirred and heated at reflux under a water separator until water is no longer collected (about 2.5 hours). The mixture is cooled to 10° C. and the precipitate of (2α,3β,4α)-(±)-3,4-dihydro-2-methyl-4-(methylamino)-2H-1-benzopyran-3-ol, hydrogen sulfate ester, is collected by filtration, washed with xylene, then with pentane, and dried at reduced pressure; m.p. 246°-247° C.

EXAMPLE 3

(1aα,2β,7bα)-(±)-1,1a,2,7b-Tetrahydro-1,2-dimethyl[1-]benzopyrano[3,4-b]azirine

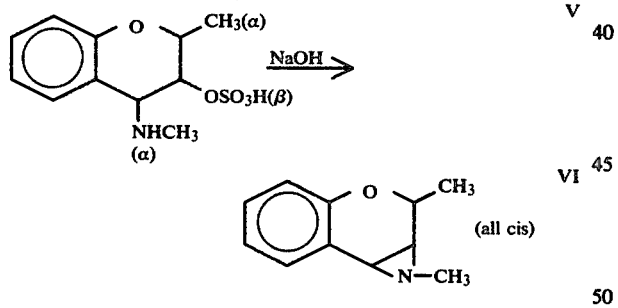

A mixture of 144 g. of (2α,3β,4α)-(±)-3,4-dihydro-2-methyl-4-(methylamino)-2H-1-benzopyran-3-ol, hydrogen sulfate ester (Example 2), and 1 l. of 2 N sodium hydroxide is stirred as the solid dissolves, followed by precipitation of the sodium salt. A nitrogen atmosphere is then provided, 200 ml. of toluene is added and the mixture is heated at 97°-98° C. for 3 hours. The organic phase is separated and the aqueous phase is extracted twice with 200 ml. portions of toluene. The combined toluene solution is dried over anhydrous potassium carbonate, treated with activated charcoal and filtered. The toluene filtrate, containing (1aα,2β,7bα)-(±)-1,1a,2,7b-tetrahydro-1,2-dimethyl[1]benzopyrano[3,4-b]azirine, may be used as such without isolation of the product. If desired, however, the azirine may be isolated by evaporation of the toluene followed by purification by distillation; b.p. 86°-88° C./0.12 mm.

EXAMPLE 4 cis-(±)-3,4-Dihydro-N,2-dimethyl-2H-1-benzopyran-3-amine

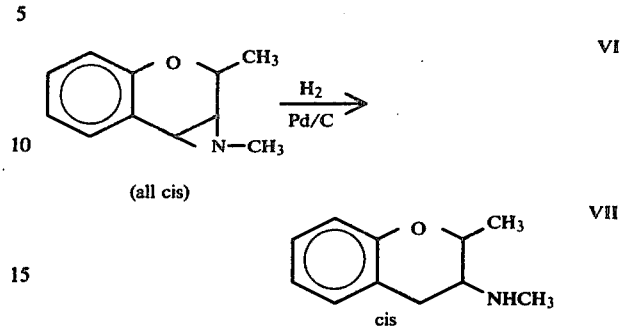

The toluene solution of (1aα,2β,7bα)-(±)-1,1a,2,7b-tetrahydro-1,2-dimethyl[1]benzopyrano[3,4-b]azirine, obtained in Example 3, is treated with 1 g. of 20% palladium on charcoal and the mixture is shaken with hydrogen at 50 p.s.i. until hydrogen uptake ceases (about 1 hour). The catalyst is removed by filtration and the filtrate is evaporated at reduced pressure. The residue is triturated with an equal volume of ether and the mixture is chilled and filtered to remove a small amount of insoluble material. The ether solution is evaporated at reduced pressure to give cis-(±)-3,4-dihydro-N,2-dimethyl-2H-1-benzopyran-3-amine, suitable for use without further purification.

The hydrochloride salt, prepared from the base and dry hydrogen chloride in 2-propanol and precipitated with ether, melts at 238.5°-240° C. The hydrobromide salt, prepared similarly, melts at 219°-220° C.

EXAMPLE 5 cis-(±)-3,4-Dihydro-N,N,2-trimethyl-2H-1-benzopyran-3-amine Monohydrochloride

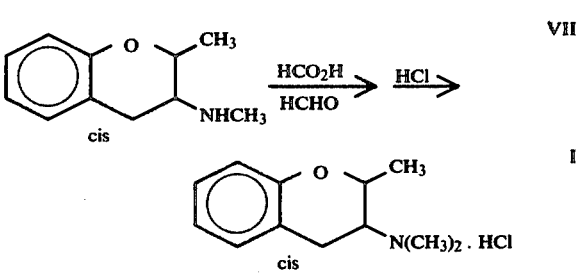

A mixture of 64 ml. of 37% aqueous formaldehyde and 135 ml. of 97-100% formic acid is cooled to 10° C. and treated slowly with stirring with 88.4 g. of cis-(±)-3,4-dihydro-N,2-dimethyl-2H-1-benzopyran-3-amine (Example 4) while maintaining the temperature below 15° C. The mixture is stirred and heated at 45°-50° C. for 20 minutes, then heated to 90° C. over a 30 minute period. The mixture is maintained at 90° until carbon dioxide evolution ceases (about 15 minutes), then cooled to 35° C. and treated with 55 ml. of concentrated hydrochloric acid and 100 ml. of methanol. The mixture is stirred for 30 minutes, then evaporated at reduced pressure. The crystalline residue is dissolved in 1.2 l. of hot 2-propanol and the solution is treated with activated charcoal and filtered. The filtrate is concentrated to a volume of 800 ml. and chilled. The resulting crystalline precipitate of cis-(±)-3,4-dihydro-N,N,2-trimethyl-2H-

We claim:

1. A process for preparing cis-(±)-3,4-dihydro-N,N,2-trimethyl-2H-1-benzopyran-3-amine having the formula I:

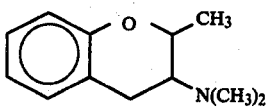

(cis)

which comprises the following steps:

1. reacting a solution of 2-methyl-2H-1-benzopyran having the formula II:

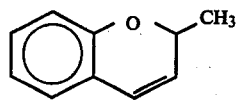

in water and a nonreactive, water-miscible solvent, with bromine to obtain, in situ, 3,4-dibromo-3,4-dihydro-2-methyl-2H-1-benzopyran having the formula IIa:

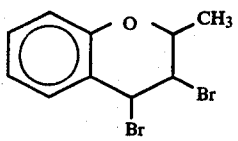

2. treating the reaction mixture of Step 1 with water and neutralizing with alkali to obtain 3,4-dihydro-3-bromo-2-methyl-2H-1-benzopyran-4-ol having the formula III:

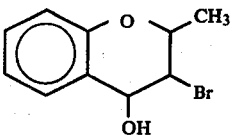

3. reacting compound III in water or a water miscible solvent with aqueous solution of methylamine to form, in situ, 3,4-epoxy-2-methylbenzopyran having the formula IIIa:

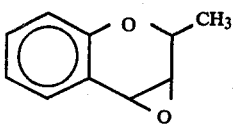

and continuing the reaction to form (2α,3β,4α)-(±)-3,4-dihydro-2-methyl-4-(methylamino)-2H-1-benzopyran-3-ol having the formula IV:

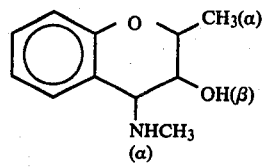

4. reacting sulfuric acid in a hydrocarbon solvent or a halogenated hydrocarbon solvent with compound IV at a temperature above 110° C. to obtain (2α,3β,4α)-(±)-3,4-dihydro-2-methyl-4-(methylamino)-2H-1-benzopyran-3-ol, hydrogen sulfate ester having the formula V:

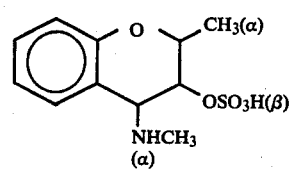

5. heating compound V and an alkali metal hydroxide to obtain (1aα,2β,7bα)-(±)-1,1a,2,7b-tetrahydro-1,2-dimethyl[1]benzopyrano[3,4-b]azirine having the formula VI:

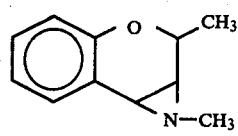

6. subjecting a solvent solution of compound VI to catalytic hydrogenation to effect ring opening and formation of cis-(±)-3,4-dihydro-N,2-dimethyl-2H-1-benzopyran-3-amine having the formula VII:

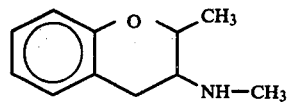

7. methylating a solvent solution of compound VII at a temperature of from about 10° C. to about 150° C. for from about 20 minutes to about 48 hours to obtain compound I in the form of the free base or the nontoxic pharmaceutically acceptable salt thereof.

2. The process according to claim 1 wherein, in Step 3, the solvent is selected from the group consisting of water, a lower alkanol, dioxane, diglyme and mixtures thereof, and the reaction is conducted at a temperature of from about 0° C. to about 100° C. for from about 1 hour to about 48 hours.

3. The process according to claim 1 wherein, in Step 3, the solvent is aqueous methanol and the reaction is conducted at a temperature of from about 20° C. to about 30° C. for from about 16 to about 30 hours.

4. The process according to claim 1 wherein, in Step 4, the solvent is selected from the group consisting of xylene, tetrachloroethane, chlorobenzene and mixtures thereof.

5. The process according to claim 1 wherein, in Step 4, the solvent is xylene and the reaction is conducted at a temperature of from about 135° C. to about 145° C. for from about 1 hour to about 3 hours.

6. The process according to claim 1 wherein, in Step 5, sodium hydroxide is used.

7. The process according to claim 1 wherein, in Step 5, there is additionally present a water immiscible, nonreactive solvent and the reaction is conducted at a temperature of from about 95° C. to about 100° C. for from about 2 to about 4 hours.

8. The process according to claim 7, wherein the reaction is conducted using sodium hydroxide with a toluene solvent.

9. The process according to claim 1 wherein, in Step 6, the solvent is selected from the group consisting of a hydrocarbon solvent; a lower alkanol; an ether selected from the group consisting of tetrahydrofuran, dioxane and diglyme; and mixtures thereof.

10. The process according to claim 1 wherein, in Step 6, the catalyst is selected from the group consisting of platinum, palladium and oxides thereof; and wherein the hydrogenation is conducted at a pressure of from about 15 to about 150 pounds per square inch.

11. The process according to claim 1 wherein, in Step 6, the catalyst is supported on a carbonacious carrier.

12. The process according to claim 1 wherein, in Step 7, the methylating agent is selected from the group consisting of a methyl halide; dimethyl sulfate; a methyl sulfonate; a formaldehyde-formic acid mixture; formaldehyde and hydrogen in the presence of a noble metal catalyst; and a trimethyloxonium salt.

13. The process according to claim 1 wherein, in Step 7, the solvent is selected from the group consisting of benzene, toluene, xylene, diethylether, dioxane, tetrahydrofuran, diglyme, methanol, ethanol, 2-propanol, acetone, 2-butanone, dimethylformamide, N-methyl-2-pyrrolidinone and mixtures thereof.

14. The process according to claim 1 wherein in Step 7, a formaldehyde-formic acid mixture is used both as the methylating agent and the solvent; and wherein the methylation is conducted at a temperature of from about 40° C. to about 100° C. for from about 30 minutes to about 6 hours.

15. A process for preparing cis-(±)-3,4-dihydro-N,2-dimethyl-2H-1-benzopyran-3-amine having the formula VII:

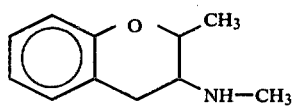

VII cis which comprises the following steps:
1. reacting a solution of 2-methyl-2H-1-benzopyran having the formula II:

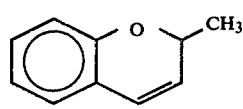

II in water and a nonreactive, water-miscible solvent, with bromine to obtain, in situ, 3,4-dibromo-3,4-dihydro-2-methyl-2H-1-benzopyran having the formula IIa:

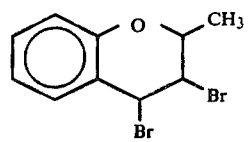

IIa 2. treating the reaction mixture of step 1 with water and neutralizing with alkali to obtain 3,4-dihydro-3-bromo-2-methyl-2H-1-benzopyran-4-ol having the formula III:

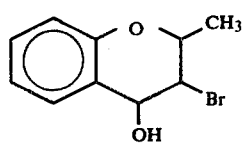

III 3. reacting compound III in water or a water miscible solvent with an aqueous solution of methylamine to form, in situ, 3,4-epoxy-2-methylbenzopyran having the formula IIIa:

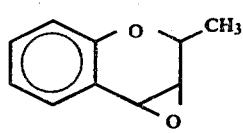

IIIa and continuing the reaction to form (2α,3β,4α)-(±)-3,4-dihydro-2-methyl-4-(methylamino)-2H-1-benzopyran-3-ol having the formula IV:

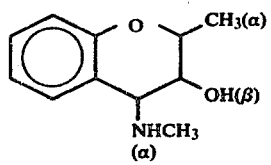

IV 4. reacting sulfuric acid in a hydrocarbon solvent or a halogenated hydrocarbon solvent with compound IV at a temperature above 110° C. to obtain (2α,3β,4α)-(±)-3,4-dihydro-2-methyl-4-(methylamino)-2H-1-benzopyran-3-ol, hydrogen sulfate ester having the formua V:

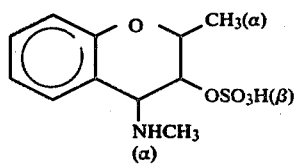

V 5. heating compound V and an alkali metal hydroxide to obtain (1aα,2β,7bα)-(±)-1,1a,2,7b-tetrahydro-1,2-dimethyl[1]benzopyrano[3,4-b]azirine having the formula VI:

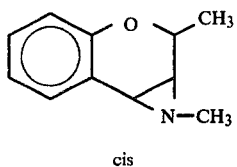

cis 6. subjecting a solvent solution of compound VI to catalytic hydrogenation to effect ring opening and formation of compound VII.

16. The process according to claim 15 wherein, in Step 3, the solvent is selected from the group consisting of water, lower alkanol, dioxane, diglyme and mixtures thereof, and the reaction is conducted at a temperature of from about 0° C. to about 100° C. for from about 1 hour to about 48 hours.

17. The process according to claim 15 wherein, in Step 3, the solvent is aqueous methanol and the reaction is conducted at a temperature of from about 20° C. to about 30° C. for from about 16 hours to about 30 hours.

18. The process according to claim 15 wherein, in Step 4, the solvent is selected from the group consisting of xylene, tetrachloroethane, chlorobenzene and mixtures thereof.

19. The process according to claim 15 wherein, in Step 4, the solvent is xylene and the reaction is conducted at a temperature of from about 135° C. to about 145° C. for from about 1 hour to about 3 hours.

20. The process according to claim 15 wherein, in Step 5, sodium hydroxide is used.

21. The process according to claim 15 wherein, in Step 5, there is additionally present a water immiscible, nonreactive solvent and the reaction is conducted at a temperature of from about 95° C. to about 100° C. for from about 2 to about 4 hours.

22. The process according to claim 21 wherein the reaction is conducted using sodium hydroxide with a toluene solvent.

23. The process according to claim 15 wherein, in Step 6, the solvent is selected from the group consisting of a hydrocarbon solvent; a lower alkanol; an ether selected from the group consisting of tetrahydrofuran, dioxane and diglyme; and mixtures thereof.

24. The process according to claim 15 wherein, in Step 6, the catalyst is selected from the group consisting of platinum, palladium, and oxides thereof; and wherein the hydrogenation is conducted at a pressure of from about 15 to about 150 pounds per square inch.

25. The process according to claim 15 wherein, in Step 6, the catalyst is supported on a carbonacious carrier.

26. A process for preparing cis-(±)-3,4-dihydro-N,N,2-trimethyl-2H-1-benzopyran-3-amine having the formula I:

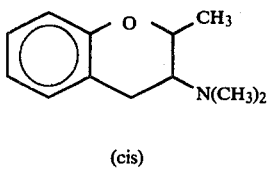

(cis)

which comprises the following steps:
1. reacting sulfuric acid in a hydrocarbon solvent or a halogenated hydrocarbon solvent with (2α,3β,4α)-(±)-3,4-dihydro-2-methyl-4-(methylamino)-2H-1-benzopyran-3-ol having the formula IV:

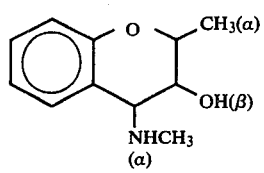

at a temperature above 110° C. to obtain (2α,3β,4α)-(±)-3,4-dihydro-2-methyl-4-(methylamino)-2H-1-benzopyran-3-ol, hydrogen sulfate ester having the formula V:

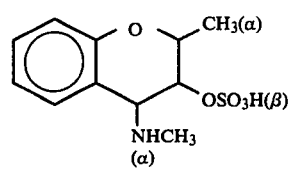

2. heating compound V and an alkali metal hydroxide to obtain (1aα,2β,7bα)-(±)-1,1a,2,7b-tetrahydro-1,2-dimethyl[1]benzopyrano[3,4-b]azirine having the formula VI:

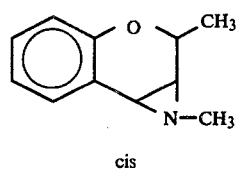

3. subjecting a solvent solution of compound VI to catalytic hydrogenation to effect ring opening and formation of cis-(±)-3,4-dihydro-N,2-dimethyl-2H-1-benzopyran-3-amine having the formula VII:

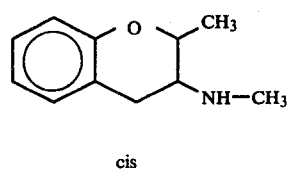

cis 4. methylating a solvent solution of compound VII at a temperature of from about 10° C. to about 150° C. for from about 20 minutes to about 48 hours to obtain compound I in the form of the free base or the nontoxic pharmaceutically acceptable salt thereof.

27. The process according to claim 26 wherein, in Step 1, the solvent is selected from the group consisting of xylene, tetrachloroethane, chlorobenzene and mixtures thereof.

28. The process according to claim 26 wherein, in Step 1, the solvent is xylene and the reaction is conducted at a temperature of from about 135° C. to about 145° C. for from about 1 hour to about 3 hours.

29. The process according to claim 26 wherein, in Step 2, sodium hydroxide is used.

30. The process according to claim 26 wherein, in Step 2, there is additionally present a water immiscible, nonreactive solvent and the reaction is conducted at a temperature of from about 95° C. to about 100° C. for from about 2 to about 4 hours.

31. The process according to claim 30, wherein the reaction is conducted using sodium hydroxide with a toluene solvent.

32. The process according to claim 26 wherein, in Step 3, the solvent is selected from the group consisting of a hydrocarbon solvent; a lower alkanol; an ether selected from the group consisting of tetrahydrofuran, dioxane and diglyme; and mixtures thereof.

33. The process according to claim 26 wherein, in Step 3, the catalyst is selected from the group consisting of platinum, palladium and oxides thereof; and wherein the hydrogenation is conducted at a pressure of from about 15 to about 150 pounds per square inch.

34. The process according to claim 26 wherein, in Step 3, the catalyst is supported on a carbonacious carrier.

35. The process according to claim 26 wherein, in Step 4, the methylating agent is selected from the group consisting of a methyl halide; dimethyl sulfate; a methyl sulfonate; a formaldehyde-formic acid mixture; formaldehyde and hydrogen in the presence of a noble metal catalyst; and a trimethyloxonium salt.

36. The process according to claim 26 wherein, in Step 4, the solvent is selected from the group consisting of benzene, toluene, xylene, diethylether, dioxane, tetrahydrofuran, diglyme, methanol, ethanol, 2-propanol, acetone, 2-butanone, dimethylformamide, N-methyl-2-pyrrolidinone and mixtures thereof.

37. The process according to claim 26 wherein in Step 4, a formaldehyde-formic acid mixture is used both as the methylating agent and the solvent; and wherein the methylation is conducted at a temperature of from about 40° C. to about 100° C. for from about 30 minutes to about 6 hours.

38. A process for preparing cis-(±)-3,4-dihydro-N,2-dimethyl-2H-1-benzopyran-3-amine having the formula VII:

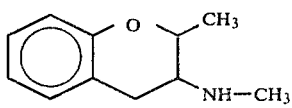

cis which comprises the following steps:
1. reacting sulfuric acid in a hydrocarbon solvent or a halogenated hydrocarbon solvent with (2α,3β,4α)-(±)-3,4-dihydro-2-methyl-4-(methylamino)-2H-1-benzopyran-3-ol having the formula IV:

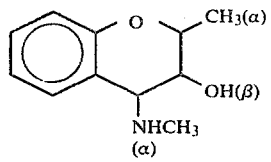

at a temperature above 110° C. to obtain (2α,3β,4α)-(±)-3,4-dihydro-2-methyl-4-(methylamino)-2H-1-benzopyran-3-ol,hydrogen sulfate ester having the formua V:

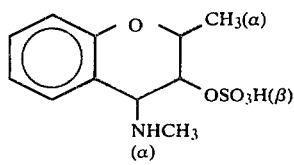

2. heating compound V and an alkali metal hydroxide to obtain (1aα,2β,7bα)-(±)-1,1a,2,7b-tetrahydro-1,2-dimethyl[1]benzopyrano[3,4-b]azirine having the formula VI:

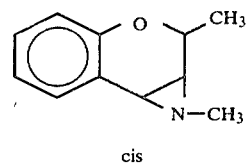

cis 3. subjecting a solvent solution of compound VI to catalytic hydrogenation to effect ring opening and formation of compound VII.

39. The process according to claim 38 wherein, in Step 1, the solvent is selected from the group consisting of xylene, tetrachloroethane, chlorobenzene and mixtures thereof.

40. The process according to claim 38 wherein, in Step 1, the solvent is xylene and the reaction is conducted at a temperature of from about 135° C. to about 145° C. for from about 1 hour to about 3 hours.

41. The process according to claim 38 wherein, in Step 2, sodium hydroxide is used.

42. The process according to claim 38 wherein, in Step 2, there is additionally present a water immiscible, nonreactive solvent and the reaction is conducted at a temperature of from about 95° C. to about 100° C. for from about 2 to about 4 hours.

43. The process according to claim 42 wherein the reaction is conducted using sodium hydroxide with a toluene solvent.

44. The process according to claim 38 wherein, in Step 3, the solvent is selected from the group consisting of a hydrocarbon solvent; a lower alkanol; an ether selected from the group consisting of tetrahydrofuran, dioxane and diglyme; and mixtures thereof.

45. The process according to claim 38 wherein, in Step 3, the catalyst is selected from the group consisting of platinum, palladium, and oxides thereof; and wherein the hydrogenation is conducted at a pressure of from about 15 to about 150 pounds per square inch.

46. The process according to claim 38 wherein, in Step 3, the catalyst is supported on a carbonacious carrier.

47. A process for preparing cis-(±)-3,4-dihydro-N,2-dimethyl-2H-1-benzopyran-3-amine having the formula VII:

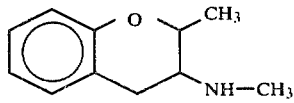

cis which comprises subjecting a solvent solution of a compound having the formula VI:

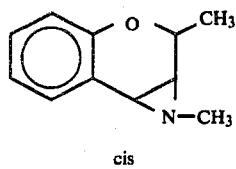

cis to catalytic hydrogenation to effect ring opening and formation of compound VII.

48. The process according to claim 47 wherein the solvent is selected from the group consisting of a hydrocarbon solvent; a lower alkanol; an ether selected from the group consisting of tetrahydrofuran, dioxane and diglyme; and mixtures thereof.

49. The process according to claim 47 wherein the catalyst is selected from the group consisting of platinum, palladium and oxides thereof; and wherein the hydrogenation is conducted at a pressure of from about 15 to about 150 pounds per square inch.

50. The process according to claim 47 wherein the catalyst is supported on a carbonacious carrier.

51. A process for preparing (1aα,2β,7bα)-(±)-1,1a,2,7b-tetrahydro-1,2-dimethyl[1]benzopyrano[3,4-b]azirine having the formula VI:

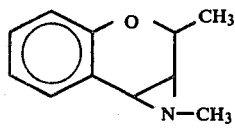

cis which comprises the following steps:

1. reacting a solution of 2-methyl-2H-1-benzopyran having the formula II:

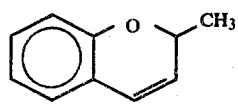

in water and a nonreactive, water-miscible solvent, with bromine to obtain, in situ, 3,4-dibromo-3,4-dihydro-2-methyl-2H-1-benzopyran having the formula IIa:

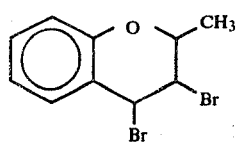

2. treating the reaction mixture of Step 1 with water and neutralizing with alkali to obtain 3,4-dihydro-3-bromo-2-methyl-2H-1-benzopyran-4-ol having the formula III:

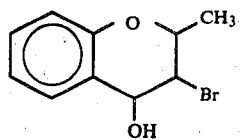

3. reacting compound III in water or a water miscible solvent with aqueous solution of methylamine to form, in situ, 3,4-epoxy-2-methylbenzopyran having the formula IIIa:

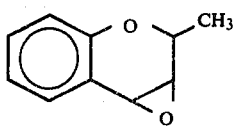

and continuing the reaction to form (2α,3β,4α)-(±)-3,4-dihydro-2-methyl-4-(methylamino)-2H-1-benzopyran-3-ol having the formula IV:

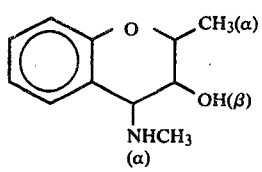

4. reacting sulfuric acid in a hydrocarbon solvent or a halogenated hydrocarbon solvent with compound IV at a temperature above 110° C. to obtain (2α,3β,4α)-(±)-3,4-dihydro-2-methyl-4-(methylamino)-2H-1-benzopyran-3-ol, hydrogen sulfate ester having the formula V:

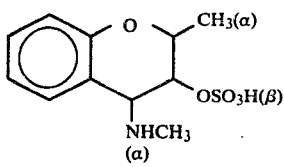

5. heating compound V and an alkali metal hydroxide to obtain (1aα,2β,7bα)-(±)-1,1a,2,7b-tetrahydro-1,2-dimethyl[1]benzopyrano[3,4-b]azirine having the formula VI.

52. The process according to claim 51, wherein, in Step 3, the solvent is selected from the group consisting of water, a lower alkanol, dioxane, diglyme and mixtures thereof, and the reaction is conducted at a temperature of from about 0° C. to about 100° C. for from about 1 hour to about 48 hours.

53. The process according to claim 51, wherein, in Step 3, the solvent is aqueous methanol and the reaction is conducted at a temperature of from about 20° C. to about 30° C. for from about 16 to about 30 hours.

54. The process according to claim 51 wherein, in Step 4, the solvent is selected from the group consisting of xylene, tetrachloroethane, chlorobenzene and mixtures thereof.

55. The process according to claim 51 wherein, in Step 4, the solvent is xylene and the reaction is conducted at a temperature of from about 135° C. to about 145° C. for from about 1 hour to about 3 hours.

56. The process according to claim 51 wherein, in Step 5, sodium hydroxide is used.

57. The process according to claim 51 wherein, in Step 5, there is additionally present a water immiscible, nonreactive solvent and the reaction is conducted at a temperature of from about 95° C. to about 100° C. for from about 2 to about 4 hours.

58. The process according to claim 57 wherein the reaction is conducted using sodium hydroxide with a toluene solvent.

59. A process for preparing (2α,3β,4α)-(±)-3,4-dihydro-2-methyl-4-(methylamino)-2H-1-benzopyran-3-ol, hydrogen sulfate ester having the formula V:

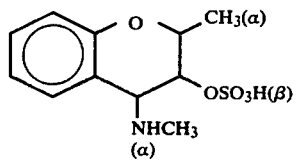

which comprises the following steps:
1. reacting a solution of 2-methyl-2H-1-benzopyran having the formula II:

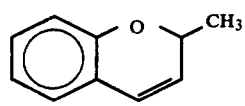

in water and a nonreactive, water-miscible solvent, with bromine to obtain, in situ, 3,4-dibromo-3,4-dihydro-2-methyl-2H-1-benzopyran having the formula IIa:

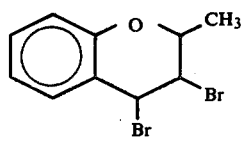

2. treating the reaction mixture of Step 1 with water and neutralizing with alkali to obtain 3,4-dihydro-3-bromo-2-methyl-2H-1-benzopyran-4-ol having the formula III:

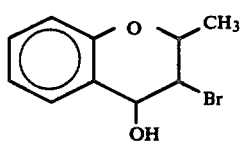

3. reacting compound III in water or a water miscible solvent with aqueous solution of methylamine to form, in situ, 3,4-epoxy-2-methylbenzopyran having the formula IIIa:

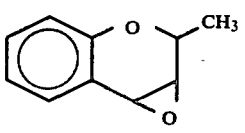

and continuing the reaction to form (2α,3β,4α)-(±)-3,4-dihydro-2-methyl-4-(methylamino)-2H-1-benzopyran-3-ol having the formula IV:

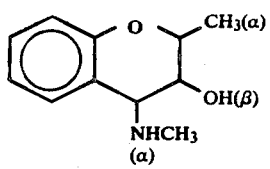

4. reacting sulfuric acid in a hydrocarbon solvent or a halogenated hydrocarbon solvent with compound IV at a temperature above 110° C. to obtain (2α,3β,4α)-(±)-3,4-dihydro-2-methyl-4-(methylamino)-2H-1-benzopyran-3-ol, hydrogen sulfate ester having the formula V.

60. The process according to claim 59, wherein, in Step 3, the solvent is selected from the group consisting of water, a lower alkanol, dioxane, diglyme and mixtures thereof, and the reaction is conducted at a temperature of from about 0° C. to about 100° C. for from about 1 hour to about 48 hours.

61. The process according to claim 59, wherein, in Step 3, the solvent is aqueous methanol and the reaction is conducted at a temperature of from about 20° C. to about 30° C. for from about 16 to about 30 hours.

62. The process according to claim 59, wherein, in Step 4, the solvent is selected from the group consisting of xylene, tetrachloroethane, chlorobenzene and mixtures thereof.

63. The process according to claim 59, wherein, in Step 4, the solvent is xylene and the reaction is conducted at a temperature of from about 135° C. to about 145° C. for from about 1 hour to about 3 hours.

64. A process for preparing (2α,3β,4α)-(±)-3,4-dihydro-2-methyl-4-(methylamino)-2H-1-benzopyran-3-ol having the formula IV:

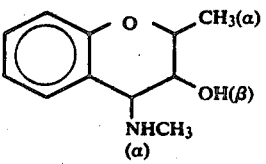

which comprises the following steps:
1. reacting a solution of 2-methyl-2H-1-benzopyran having the formula II:

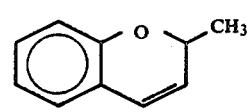

in water and a nonreactive, water-miscible solvent, with bromine to obtain, in situ, 3,4-dibromo-3,4-dihydro-2-methyl-2H-1-benzopyran having the formula IIa:

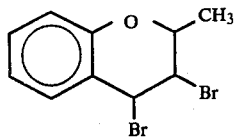

2. treating the reaction mixture of Step 1 with water and neutralizing with alkali to obtain 3,4-dihydro-3-bromo-2-methyl-2H-1-benzopyran-4-ol having the formula III:

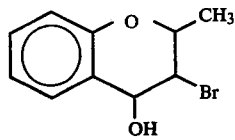

3. reacting compound III in water or a water miscible solvent with aqueous solution of methylamine to form, in situ, 3,4-epoxy-2-methylbenzopyran having the formula IIIa:

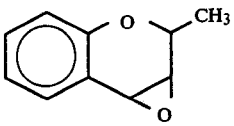

and continuing the reaction to form $(2\alpha,3\beta,4\alpha)$-$(\pm)$-3,4-dihydro-2-methyl-4-(methylamino)-2H-1-benzopyran-3-ol having the formula IV.

65. The process according to claim 64, wherein, in Step 3, the solvent is selected from the group consisting of water, a lower alkanol, dioxane, diglyme and mixtures thereof, and the reaction is conducted at a temperature of from about 0° C. to about 100° C. for from about 1 hour to about 48 hours.

66. The process according to claim 64, wherein, in Step 3, the solvent is aqueous methanol and the reaction is conducted at a temperature of from about 20° C. to about 30° C. for from about 16 to about 30 hours.

* * * * *